United States Patent [19]

Jaeger

[11] 4,116,635

[45] Sep. 26, 1978

[54] GENERAL PURPOSE IN VITRO ANTICOAGULANT

[76] Inventor: Mark A. Jaeger, 110 Betty Jean La., Lemay, Mo. 63125

[21] Appl. No.: 777,147

[22] Filed: Mar. 14, 1977

[51] Int. Cl.² ........................................... G01N 33/16
[52] U.S. Cl. ........................... 23/230 B; 195/103.5 R; 424/101
[58] Field of Search ............... 23/230 B; 195/103.5 R; 260/534 E; 424/1

[56] References Cited

U.S. PATENT DOCUMENTS

| | | | |
|---|---|---|---|
| 3,682,835 | 8/1972 | Louderback | 23/230 B X |
| 3,799,885 | 3/1974 | Dennis | 23/230 B X |
| 3,852,344 | 12/1974 | Bragdon | 260/534 E |
| 3,859,337 | 1/1975 | Herz | 260/534 E X |
| 3,947,378 | 3/1976 | Babson | 23/230 B X |
| 3,983,004 | 9/1976 | Trobisch | 23/230 B X |

*Primary Examiner*—Sidney Marantz
*Attorney, Agent, or Firm*—Gravely, Lieder & Woodruff

[57] ABSTRACT

A process for testing a blood sample as for coagulation, hematology, chemistries, enzymes, electrolytes and trace metals which involves the addition of a particular anticoagulant. The anticoagulant is a calcium chelating agent having a Log K' of from about 3.4 to 4.2.

10 Claims, No Drawings

GENERAL PURPOSE IN VITRO ANTICOAGULANT

BACKGROUND OF THE INVENTION

Twentieth century blood testing work has evolved into separate, specialized areas such as:

Coagulation
Hematology
Blood chemistries and enzymes
Electrolytes and trace metals
Serology Present techniques for blood analysis require the use of different anticoagulants for different analyses of in vitro blood samples. These anticoagulants are chosen for optimum effect in specific uses, and are seldom interchangeable.

The in vitro anticoagulants in use at present are of two types:

(1) antithrombins, such as heparin,
(2) those that remove calcium ions from the blood to prevent coagulation, such as citrate, oxalate, fluoride, and ethylene diamine tetra acetic acid (EDTA).

In coagulation studies, calcium ion must be prevented from initiating a coagulation reaction in freshly drawn blood samples. Plasma is separated from red cells and then recalcified under controlled conditions. The most commonly used anticoagulant for in vitro coagulation studies is citric acid. It is generally employed in the form of sodium citrate. EDTA is not used in coagulation procedures because abnormally high coagulation times are obtained upon recalcification of EDTA plasmas. Oxalate, fluoride, heparinized plasma, and serum are of little or no use in coagulation studies.

Ethylene diamine tetra acetic acid (EDTA) is the preferred in vitro anticoagulant for hematology studies. It is usually employed in the form of the sodium or potassium salt. Sodium citrate is not used in hematology procedures because cell morphology is altered, and some platelets are destroyed in citrated blood. Unanticoagulated whole blood may be used for making stained blood smears for microscropic examination of cell morphology; heparin may be used as an anticoagulant for all hematological tests except morphology, because anionic heparin reacts with the cationic dye used for staining blood smears. Fluoride and oxalate have limited use.

The chief requirement for a fluid medium for testing in the areas of blood chemistries, enzymes, electrolytes, and trace metals is that the test medium contain no ingredient that will interfere with the tests being conducted. Serum or heparinized plasma are the desired media. However, serum potassium values are often high, due to potassium released into serum by platelets and red cells during the coagulation process; heparin plasmas often yield false high phosphorus results, and bring about enzyme inhibition.

Citrated of EDTA plasmas often result in errors in calcium determinations and alkaline phosphatase determinations. Oxalate and fluoride anticoagulants also result in interference in many of these determinations.

It is an object of this invention to provide an in vitro anticoagulant which can be used in coagulation and hematology determinations, but which will not interfere with chemistries, enzymes, electrolytes or trace metals.

The stability constant, K, for a metal chelate is the ratio of chelated metal ions in a solution at equilibrium to that of unchelated metal ions. For calcium chelates, the stability constant may be expressed as follows:

$$K = \frac{\text{Ca chelate}^-}{(\text{Ca}^{++})(\text{Chelate}^{---})}$$

Since K is usually a very high number, log K is the favored expression in the technical literature. Stability constants for the calcium chelates under consideration are:

| | |
|---|---|
| Citric Acid | log K = 3.2 |
| EDTA | log K = 10.7 |

Coagulation times increase as the value of K increases. In the art of blood testing work, it is common to encounter the symbol K', the conditional calcium salt stability at pH 7.5. The pH value of 7.5 is the pH level of blood plasma at 25° C. As coagulation times increase, the value of K', like the value of K, increases. A chelate having a log K' of 3 is sufficiently low in stability to permit plasma recalcification for coagulation studies, but not sufficiently high in stability to permit hematological studies. A chelate having a log K' appreciably higher than 4 is sufficiently high in stability to permit use in hematological studies, but not sufficiently low in stability to permit recalcification for coagulation studies.

I have discovered that the use of certain compounds having calcium salt stability constant of log K' of about 3.4 to about 4.2, preferably about 4, namely N-(2-acetamido)-imino diacetic acid, and hydroxyethyl imino diacetic acid, and alkali metal or alkaline buffer salts of these compounds will permit dual use as an in vitro anticoagulant in coagulation studies and in hematology studies. The alkali metal salts that are suitable in this invention are potassium, sodium, and lithium salts. The alkaline buffer salts that are suitable are Imidazole and Tris salts.

At calcium salt stability of log K' of 4, these selected compounds yield coagulation results similar to those yielded by conventional sodium citrate anticoagulants. The compounds also yield hematological results similar to those yielded by conventional EDTA anticoagulants.

Faust et al., U.S. Pat. No. 2,193,717 claims a process for preventing the congealing of blood by using a water-soluble amino acid containing in the molecule more than one organic radical having a carboxylic group on each basic nitrogen atom; more specifically, it calls for the use of either the sodium salt of nitrilo-triacetic acid or the sodium salt of ethylene-bis (imino-diacetic acid) (EDTA).

EDTA will not permit the coagulation testing that the chelates of my invention will permit. EDTA is effective for hematology studies, but is undesirable for coagulation studies. Nitrilo-triacetic acid, although rarely used as an in vitro anticoagulant, is effective for hematology studies, but is ineffective for coagulation studies.

At the present time, a minimum of three blood samples is required for a complete patient profile in coagulation, hematology, and blood chemistry. A citrated sample is required for coagulation, an EDTA anticoagulated sample is required for hematology, and an unanticoagulated sample is required to obtain serum for blood chemistry. Although volumes of blood drawn for the first two samples are usually of 5 ml or 7 ml, only a few tenths of a milliliter is used for testing. This procedure is merely wasteful for robust donors who are sampled infrequently, but it presents a serious problem in obtaining valid samples from pediatric or geriatric patients, who often must be tested frequently.

Frequent, repeated sampling of the pediatric or geriatric patient often results in partial collapse of the vein during blood sample withdrawal, and consequent hemolysis of blood samples. Hemolyzed EDTA blood samples may be used for most hematology testing, with the exception of red cell fragility; hemolyzed serum samples will give falsely high readings from iron, potassium, triglycerides, transaminase enzymes, and lactate dehydrogenase; hemolyzed citrated samples are worthless for coagulation studies.

SUMMARY OF THE INVENTION

This invention involves calcium chelates which inhibit coagulation of in vitro blood samples.

The coagulation inhibition is brought about through the use of certain chelating agents of a selected stability, making it possible for a clinician to perform coagulation and hematology testing with a single blood sample. These chelates are dissolved in alkaline buffers to produce salts that do not interfere with blood chemistry or electrolyte determinations, thus permitting general use.

DETAILED DESCRIPTION

A variety of tests can be carried out with a given sample of blood by adding the blood to a tube containing the specified compounds of this invention.

Suitable compounds are N-(2-acetamido)-imino diacetic acid or ADA, sodium ADA, potassium ADA, lithium ADA, Tris ADA or Imidazole ADA. Approximately 0.5 to about 2.0 mg of the foregoing acids or salts of these acids per ml of blood are added to a glass or plastic tube. The prescribed amount of blood is then added to the tube, the ADA is dissolved in the blood, and the desired tests can then be performed.

The following examples will show
(1) hematology and coagulation results obtained by using a compound in the class of compounds of this invention;
(2) blood chemistry and enzyme determination results from plasmas obtained by using a compound of this invention, compared to results obtained by using serum;
(3) metal analyses run on an aqueous solution of a compound of this invention combined with Imidazole and with Tris, showing the lack of interference to be expected when used in these analyses in blood studies;
(4) alkaline phosphatase results by using a compound of this invention combined with Imidazole and with Tris, showing interference by the compound with a given method of analysis.

EXAMPLE I

Seven different chelating agents were compared in this example. These agents were:
(1) Ethylene diamine tetra acid (EDTA)
(2) Hydroxyethyl ethylene diamine triacetic acid (HEDTA)
(3) Nitrilotriacetic acid (NTA)
(4) Eriochrome black T (EBT)
(5) N-(2-acetamido)-imino diacetic acid (ADA)
(6) Methyl imino diacetic acid (MDA)
(7) Sodium citrate Ten mg of EDTA were added to a clean test tube. Ten mg of HEDTA were added to a second clean test tube. Ten mg each of NTA, EBT, ADA, and MDA were added to third, fourth, fifth, and sixth test tubes. Twenty mg of sodium citrate dihydrate dissolved in 0.5 ml of water were added to a seventh clean test tube. Blood from a single donor was collected into each tube. The volume of blood collected into each of the first six tubes was 7 ml and the volume of blood collected into the seventh tube was 4.5 ml. All the tubes were stoppered and inverted gently 10 times to mix the contents. The tubes were allowed to stand for 30 minutes so that clotting of blood could take place in the tubes that did not contain true in vitro anticoagulants. After the contents of the tubes were mixed again, whole blood samples were removed when possible, to determine hematocrit and platelet count, and to make a blood smear for staining and microscopic examination of cell morphology. The whole blood samples were then centrifuged to obtain plasma for use in the coagulation determinations of prothrombin time and activated partial thromboplastin time. The results are tabulated in Table I.

TABLE I

| | CALCIUM SALT | | HEMATOLOGY | | | COAGULATION | |
|---|---|---|---|---|---|---|---|
| | | | a | b | | c | d |
| Chelate | Log K | Log K' | HCT | Platelets | Morphology | PT-1 | APTT |
| EDTA | 10.7 | 7.9 | 51 | 246,000 | Normal | 15.6 | 39.2 |
| HEDTA | 8.0 | 5.8 | 52 | 248,000 | Normal | 14.0 | 35.8 |
| NTA | 6.4 | 4.2 | 49 | 247,000 | Normal | 12.7 | 29.4 |
| EBT | 5.4 | 1.4 | — | — | Clotted | — | — |
| ADA | 4.0 | 4.0 | 51 | 248,000 | Normal | 10.4 | 25.4 |
| MDA | 3.8 | 1.7 | — | — | Clotted | — | — |
| Sodium Citrate | 3.2 | 3.2 | 46 | 198,000 | Altered | 10.4 | 26.5 | a HCT: Percent Hematocrit
b PLATELETS: Count Per mm$^3$
c PT-1: Prothrombin Time, Seconds
d APTT: Activated Partial Thromboplastin Time, Seconds Although log K values for EBT and MDA are 5.4 and 3.8, respectively, the log K' (pH-7.5) values are only 1.4 and 1.7 respectively. Log K' is the conditional stability constant at pH of 7.5, the pH value of blood at room temperature. At log K' values of 1.4 and 1.7, the calcium salt stability constants are too low to prevent clotting. The hematology values from the sodium citrate sample are unsatisfactory, and the coagulation values for the EDTA, HEDTA, and NTA plasmas have approached abnormal values.

EXAMPLE II

Two tubes were prepared, one of which contained 10 mg of Imidazole in 100 microliters of water, the other of which contained 10 mg Tris [Tris (hydroxy methyl) amino methane] in 100 microliters of water. Ten mg of N-(2-acetamido)-imino diacetic acid (ADA) were then dissolved in each of the tubes.

Blood from a single donor was collected into each tube, and into a third empty tube. The total volume in each of the tubes was 7 ml. The first two tubes were stoppered and inverted gently 10 times to mix the contents. The tubes were allowed to stand for 30 minutes so that clotting of the blood could take place in the tube not containing anticoagulant. The tubes were then centrifuged for 10 minutes to separate blood plasma from the red cells in the first two tubes, and to separate blood serum from clotted red cells in the third tube.

The plasmas and serum were removed from the tubes and subjected to common blood chemistry and enzyme determinations. The results are tabulated in Table II.

TABLE II

| Determination | Units | Serum | ADA/Imidazole | ADA/Tris |
|---|---|---|---|---|
| Chemistries | | | | |
| Glucose | mg/dl | 67 | 67 | 67 |
| Urea Nitrogen | mg/dl | 16.7 | 16.6 | 16.1 |
| Uric Acid | mg/dl | 6.7 | 6.7 | 6.7 |
| Cholesterol | mg/dl | 182 | 181 | 179 |
| Bilirubin | mg/dl | 0.4 | 0.4 | 0.4 |
| Creatinine | mg/dl | 1.0 | 1.0 | 1.0 |
| Total Protein | gm/dl | 7.5 | 7.8 | 7.4 |
| Triglycerides | mg/dl | 154 | 158 | 158 |
| Inorganic Phosphorus | mg/dl | 4.1 | 3.8 | 3.8 |
| Calcium | mg/dl | 8.9 | 9.4 | 9.1 |
| Chloride | meg/L | 99 | 95 | 95 |
| Albumin | gm/dl | 4.2 | 4.2 | 4.2 |
| Enzymes | | | | |
| Cholinesterase | U/ml | 45 | 47 | 46 |
| Lactate Dehydrogenase | U/ml | 125 | 125 | 115 |
| Creatine Phosphokinase | mU/ml | 50 | 44 | 46 |
| Hydroxybutyric Dehydrogenase | U/ml | 105 | 105 | 105 |
| Glutamic Oxalacetic Transaminase | U/ml | 16 | 16 | 16 |
| Glutamic Pyruvic Transaminase | U/ml | 20 | 22 | 20 |

No interference or analytical problems were apparent in the foregoing determinations.

EXAMPLE III

Two tubes were prepared as in Example II, one of which contained 10 mg of Imidazole and 10 mg of ADA dissolved in 100 microliters of water, and the other of which contained 10 mg of Tris and 10 mg of ADA dissolved in 100 microliters of water.

Seven ml of deionized water were collected in each tube. The tubes were stoppered and inverted 10 times to thoroughly mix the contents. The amounts of various electrolytes and trace metals were then measured by atomic absorption spectrophotometry to determine the interfering substances present in the anticoagulants which would prove detrimental to analyses for the electrolytes and trace metals. The results are tabulated in Table III.

TABLE III

| Electrolyte | serum/Plasma Normal Range | Units | ADA/Imidazole | ADA/Tris |
|---|---|---|---|---|
| Sodium | 310–356 | mg/dl | 0.24 | 0.25 |
| Potassium | 14–21.5 | mg/dl | 0.02 | 0.02 |
| Lithium | | mg/dl | 0.001 | 0.001 |
| Calcium | 9–11.5 | mg/dl | 0.06 | 0.07 |
| Magnesium | 1.8–2.9 | mg/dl | 0.01 | 0.01 |
| Zinc | .055–.150 | mg/dl | 0.002 | 0.002 |
| Iron | .065–.175 | mg/dl | 0.005 | 0.002 |
| Copper | .070–.155 | mg/dl | 0.002 | 0.002 |
| Lead | 080 | mg/dl | 0.002 | 0.002 |

The amounts of impurities present in the anticoagulants at normal dilution are at such a level as to provide no interference or false positive readings in any of the metal determinations listed above.

EXAMPLE IV

The following example illustrates an area in which the compounds of this invention cause interference with an analytical procedure.

Two procedures were employed for the determination of alkaline phosphatase. Both procedures require the presence of unchelated magnesium ion for completion of the reaction; consequently, because both EDTA plasma and citrate plasma will chelate magnesium, these compounds are undesirable for alkaline phosphatase determinations. ADA is also a magnesium chelating agent, but its magnesium chelate stability is lower than that of citrate or EDTA.

The first procedure (A) hydrolyzes p-nitrophenyl phosphate into p-nitrophenol and phosphate, and measures the amount of p-nitrophenol produced. The second procedure (B) hydrolyzes thymolphthalein monophosphate into thymolphthalein and phosphorus, and measures the amount of thymolphthalein produced.

ADA/Imidazole and ADA/Tris tubes were prepared as in Example II. Blood was collected from a number of donors. Serum tubes were used as controls. The results are tabulated in Table IV.

TABLE IV

| Donor | Method | Serum | ADA/Imidazole | ADA/Tris |
|---|---|---|---|---|
| 1 | A | 154 mU/ml | 42 mU/ml | 75 mU/ml |
| 2 | A | 63 mU/ml | 21 mU/ml | 32 mU/ml |
| 3 | A | 60 mU/ml | 17 mU/ml | 35 mU/ml |
| 4 | A | 68 mU/ml | 18 mU/ml | 35 mU/ml |
| 5 | B | 34 U/L | 31 U/L | 32 U/L |
| 6 | B | 32 U/L | 32 U/L | 32 U/L |
| 7 | B | 36 U/L | 35 U/L | 35 U/L |

ADA, and possibly Imidazole, interfere with procedure A. There is no evidence of interference with procedure B.

What is claimed is:

1. In a process for testing a sample of blood for coagulation, hematology, chemistries, enzymes, electrolytes, and trace metals wherein said sample is introduced into a vessel containing an anticoagulant, the improvement comprising selecting for the anticoagulant a calcium chelating agent having a Log K' from about 3.4 to about 4.2, where Log K' is the logarithm of the conditional stability constant at pH 7.5.

2. The process of claim 1 wherein the calcium chelating agent is selected from the group consisting of imino deacetic acids, alkaline buffer salts of imino diacetic acids, and alkali metal salts of imino diacetic acids.

3. The process of claim 2 wherein the calcium chelating agent is N-(2-acetamido)-imino diacetic acid.

4. The process of claim 2 wherein the calcium chelating agent is hydroxyethyl imino diacetic acid.

5. The process of claim 2 wherein the calcium chelating agent is an alkaline buffer salt of N-(2-acetamido)-imino diacetic acid selected from the group consisting of Imidazole and Tris.

6. The process of claim 2 wherein the calcium chelating agent is an alkali metal salt of N-(2-acetamido)-imino diacetic acid selected from the group consisting of potassium, sodium, and lithium.

7. The process of claim 2 wherein the calcium chelating agent is an alkaline buffer salt of hydroxyethyl imino diacetic acid selected from the group consisting of Imidazole and Tris.

8. The process of claim 2 wherein the calcium chelating agent is an alkali metal salt of hydroxyethyl imino diacetic acid selected from the group consisting of potassium, sodium, and lithium.

9. The process of claim 1 wherein about 0.5 to about 2.0 mg of calcium chelating agent per ml of blood is used.

10. The process of claim 1 wherein about 2.5 to about 10.0 micromoles of calcium chelating agent per ml of blood is used.

* * * * *